US011260157B2

(12) United States Patent
Matheis

(10) Patent No.: US 11,260,157 B2
(45) Date of Patent: Mar. 1, 2022

(54) OXYGENATOR COMPRISING A HEATING ELEMENT

(71) Applicant: Xenios AG, Heilbronn (DE)

(72) Inventor: Georg Matheis, Heilbronn (DE)

(73) Assignee: Xenios AG, Heilbronn (DE)

( * ) Notice: Subject to any disclaimer, the term of this patent is extended or adjusted under 35 U.S.C. 154(b) by 521 days.

(21) Appl. No.: 16/323,812

(22) PCT Filed: Jul. 6, 2017

(86) PCT No.: PCT/DE2017/000147
§ 371 (c)(1),
(2) Date: Feb. 7, 2019

(87) PCT Pub. No.: WO2018/028726
PCT Pub. Date: Feb. 15, 2018

(65) Prior Publication Data
US 2019/0167882 A1 Jun. 6, 2019

(30) Foreign Application Priority Data
Aug. 8, 2016 (DE) ...................... 10 2016 009 534.2

(51) Int. Cl.
*A61M 1/16* (2006.01)
*A61M 1/36* (2006.01)
(52) U.S. Cl.
CPC ........ *A61M 1/1698* (2013.01); *A61M 1/1601* (2014.02); *A61M 1/1629* (2014.02);
(Continued)

(58) Field of Classification Search
CPC .............. A61M 1/3698; A61M 1/1601; A61M 1/1629; A61M 1/1664; A61M 1/369;
(Continued)

(56) References Cited

U.S. PATENT DOCUMENTS 3,112,746 A 12/1963 Gewecke et al.
3,211,148 A 10/1965 Galajda, Jr.
(Continued)

FOREIGN PATENT DOCUMENTS

CN 101691219 A 4/2010
CN 103501834 A 1/2014
(Continued)

OTHER PUBLICATIONS

International Search Report in PCT/DE2017/000147, dated Dec. 22, 2017.

*Primary Examiner* — Philip R Wiest
(74) *Attorney, Agent, or Firm* — Collard & Roe, P.C.

(57) ABSTRACT

The invention relates to an oxygenator with a housing wall, defining a housing chamber with a blood inlet and a blood outlet, a gas inlet and a gas outlet, and also with a heating element which is arranged in the oxygenator between the blood inlet and blood outlet in order to control the temperature of the blood flowing through the housing chamber. The oxygenator also comprises an electric connection and the heating element has an electric resistor which is designed as a wire. The invention also relates to a method for controlling the heat emission at the heating element of an oxygenator by measuring the flow of blood through the oxygenator and the power of a pump influencing the flow, with the heating power being adjusted in accordance therewith.

21 Claims, 4 Drawing Sheets

Figure 1:
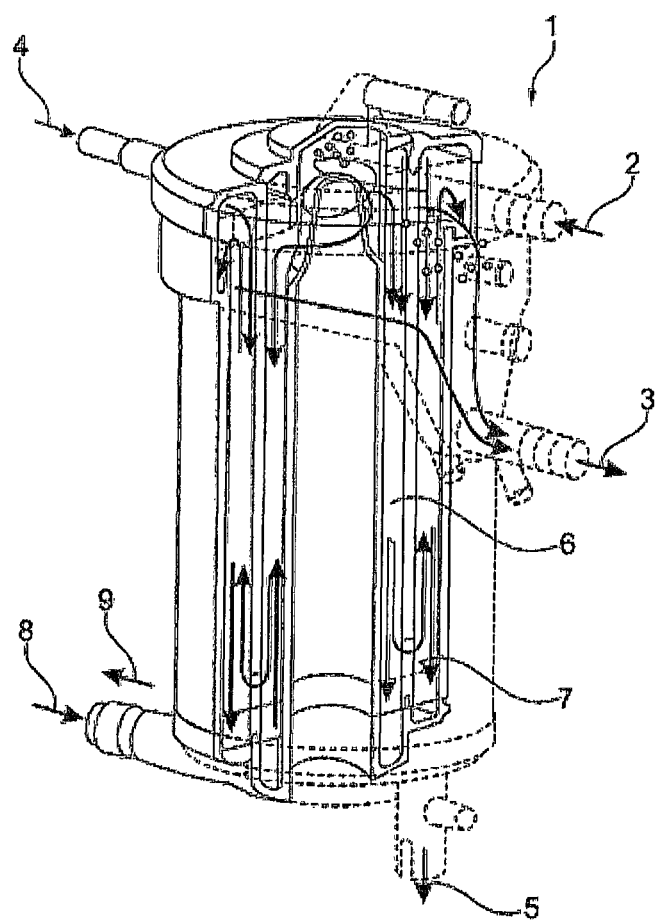

(52) U.S. Cl.
CPC .......... *A61M 1/1664* (2014.02); *A61M 1/369* (2013.01); *A61M 2205/3334* (2013.01); *A61M 2205/3368* (2013.01); *A61M 2205/3633* (2013.01); *A61M 2205/3653* (2013.01); *A61M 2205/3673* (2013.01)

(58) Field of Classification Search
CPC .. A61M 2205/3334; A61M 2205/3368; A61M 2205/3633; A61M 2205/3653; A61M 2205/3673; A61M 1/1698; A61M 1/26; A61M 1/267
See application file for complete search history.

(56) References Cited

U.S. PATENT DOCUMENTS

| | | | |
|---|---|---|---|
| 3,929,414 | A | 12/1975 | Leonard |
| 4,948,560 | A | 8/1990 | Deguchi et al. |
| 5,817,279 | A | 10/1998 | Eilers et al. |
| 7,153,285 | B2 | 12/2006 | Lauman et al. |
| 8,865,067 | B2 | 10/2014 | Olson et al. |
| 2012/0277654 | A1* | 11/2012 | Olson ................. A61M 1/3627 604/6.09 |
| 2015/0150715 | A1* | 6/2015 | Svitek ................... A61M 1/369 422/46 |
| 2016/0220748 | A1* | 8/2016 | Pouchoulin ......... A61M 1/3621 |
| 2017/0071782 | A1* | 3/2017 | Svitek .................... A61F 7/007 |

FOREIGN PATENT DOCUMENTS

| | | |
|---|---|---|
| DE | 1 096 554 B | 1/1961 |
| DE | 10 2011 052188 A1 | 1/2013 |
| EP | 0 621 047 A2 | 10/1994 |
| EP | 0 765 683 B1 | 7/1997 |
| EP | 2 143 453 A2 | 1/2010 |
| EP | 2 848 269 A1 | 3/2015 |
| WO | 2004/105589 A2 | 12/2004 |
| WO | 2012/013925 A2 | 2/2012 |
| WO | 2013/012776 A1 | 1/2013 |

* cited by examiner

OXYGENATOR COMPRISING A HEATING ELEMENT

CROSS REFERENCE TO RELATED APPLICATIONS

This application is the National Stage of PCT/DE2017/000147 filed on Jul. 6, 2017, which claims priority under 35 U.S.C. § 119 of German Application No. 10 2016 009 534.2 filed on Aug. 8, 2016, the disclosure of which is incorporated by reference. The international application under PCT article 21(2) was not published in English.

The invention relates to an oxygenator with a housing wall, defining a housing chamber with a blood inlet, a blood outlet, a gas inlet and a gas outlet, and with a heating element which is arranged in the oxygenator between the blood inlet and blood outlet in order to control the temperature of the blood flowing through the housing chamber.

Oxygenators are medical gas exchangers which are used primarily in heart-lung therapies lasting several days or in operations. A further application is dialysis, for example. These oxygenators, besides the gas exchange, often also offer the possibility of controlling the temperature of the blood flowing through a housing chamber of the oxygenator. The blood is generally heated in the oxygenator since the blood temperature in the extracorporeal circuit, that is to say outside the patient's body, decreases over time and reduces the patient's temperature. Besides this heating there is also the possibility, when performing operations on the heart, to cool the temperature of the blood so as to reduce the body temperature.

Heater-coolers (HC devices) are used in order to regulate the blood and body temperature of a patient during an operation or relatively long therapies utilising gas exchangers. A heater-cooler (HC device) is an external device that is connected to an oxygenator via tubes. Water is conducted through metal rods in the HC device and is heated or cooled. The water is then conducted to the oxygenator and flows through heat exchanger mats made of hollow fibres or through special, usually metallic conduits in the oxygenator, past which the blood is guided. An oxygenator of this kind is described in EP 765 683 B1.

Oxygenators of this kind are in practical use. The used heater-cooler devices, however, work with a water bath, which becomes dirty during use and can contaminate the air in the surrounding environment. The HC devices are very heavy and immobile due to the water bath and the cooler device. They have to be regularly cleaned since they are used in the vicinity of the oxygenator and thus in a hospital, for example in operating theatres or intensive care units.

The object of the invention is therefore to further develop an oxygenator.

This object is achieved with an oxygenator according to the invention which has an electric connection and in which the heating element has an electric resistor.

The invention is based on the finding that it is not sufficient to heat the flow of blood or gas at the blood inlet or gas inlet or at the blood outlet or gas outlet, and that a heating in the oxygenator between blood inlet and blood outlet by means of fluid-conducting pipes requires complex auxiliary equipment. Since the heating element in the oxygenator has an electric resistor, the resistor of the heating element can be used to heat the heating element by means of the electric connection on the oxygenator by way of an applied voltage. Since the electric resistor is used for heating, it is possible to dispense with an HC device, and only a voltage source is required.

The heating element can be arranged in the outer wall of the oxygenator in order to heat blood flowing in the housing chamber. It is particularly advantageous, however, if the heating element is arranged in the housing chamber. This makes it possible to use larger heating surfaces and thus to achieve a small temperature difference between the heating element and blood. Damage to the blood is thus avoided.

Depending on the purpose, however, the heating element can also be arranged in the housing wall. This enables a simple design and, in particular in the case of planar hollow fibre mats arranged in parallel, a good transfer of heat from the heating element to the blood.

Semipermeable materials, such as membranes in particular, are arranged between the gas regions and the blood regions of the oxygenator. These membranes can be planar films or hollow fibres.

In order to hold planar or tubular membranes in an oxygenator, encapsulation materials, for example made from plastic, are used. It is therefore advantageous if the oxygenator has an encapsulation layer for holding fluid lines and the heating element is arranged in this encapsulation layer or at least also in this encapsulation layer.

When heating blood it must be ensured that no blood damage occurs, also by an overheating of the blood only in regions. It is therefore proposed that the oxygenator has at least one temperature sensor. It is particularly advantageous if temperature sensors are provided in the oxygenator at various points so as to ensure that excessively high temperatures do not occur in any region. The temperature sensors, where possible, should therefore also be arranged at least in regions in which a slower blood flow rate than in other regions of the housing chamber is present, or in which a slower blood flow rate than the mean blood flow rate in the housing chamber is present, and where therefore there may be a risk of overheating.

The temperature of the heating element can be varied via the voltage applied to the heating element, and it is therefore expedient if the oxygenator has a temperature control device.

It is advantageous if the temperature at one or more points is measured at specific time intervals. The frequency can be predefined by an algorithm. Risky overheating can thus be avoided. Reference is made here to pulse width modulation.

In many cases the oxygenator is connected to a console, via which for example the flow of gas or blood through the oxygenator can be controlled. A console of this kind is a control electronics unit for open-loop or closed-loop control of the oxygenator use. By means of a console of this kind, the heating element can thus also be actuated, and this actuation can be controlled depending on other data or method parameters available at the console, such as blood or gas flow and the temperature in the oxygenator.

A particularly advantageous variant provides that the temperature controller sets or controls the temperature of the heating element individually at various locations. This makes it possible to provide heating at different points with different intensity on the basis of the usual flow rates in the oxygenator.

For this purpose it is provided that the heating element delivers a different heating power at different locations in the housing chamber. The heating power can be varied depending on the blood flow, blood velocity, gas flow and gas velocity.

One variant provides that the heating element has a plurality of heating sub-elements positionable at various locations of the oxygenator. These heating sub-elements can then be individually actuated separately from one another so as to attain a certain heating intensity distribution in the oxygenator and to modify this as applicable, also during operation of the oxygenator.

A heating element, however, can also be provided, which has a plurality of heating sub-elements actuatable separately from one another.

An additional effect is attained in that the heating element is arranged in the oxygenator between the gas inlet and gas outlet so as to also control the temperature of gas flowing through the housing chamber. Above all, condensate formation can thus also be avoided.

A simple embodiment of an oxygenator provides an oxygenator having a housing wall which has only four outwardly leading fluid passages. Of these, two fluid passages can be used for the gas inlet and gas outlet, and two fluid passages can be used for the blood inlet and blood outlet.

A connector refers to a possibility for connecting hoses to the oxygenator. Part of the heating element can be arranged in a connector of this kind.

It is advantageous if the oxygenator has a heat-conducting arrangement for conducting heat to the heating element. If the heating element is formed for example as a heatable metal part, this can be surrounded by a heat-conducting arrangement in order to enlarge the surface or to prevent contact between the blood and metal part. This heat-conducting arrangement then conducts the heat from the heating element to a surface that is in contact with the blood and is preferably larger than the surface of the heating element. A surface of this kind can be the surface of a net or a film.

The heat-conducting arrangement should be used in particular to enable a distribution of heat from the heating element in the housing chamber.

An advantageous variant provides that the oxygenator has an insulation layer or a vacuum layer so as to insulate blood flowing in the housing chamber. An insulation layer and a reflection layer can also be designed such that said layer can be opened, so as to also easily dissipate heat again so as to cool the oxygenator and thus avoid overheating. In addition, the layers also can be arranged partially or can be arrangeable partially.

In order to reflect heat radiation from blood flowing in the housing chamber back to the blood and thus also minimise the emission of heat radiation at the oxygenator, it is proposed that the oxygenator has a reflection layer. A reflection layer of this kind can be a metal foil or a polished surface, for example.

In order for the blood flow in the oxygenator to be monitored it is advantageous if the insulation, vacuum and/or reflection layer is transparent or at least partially transparent. For this purpose, a close-meshed net, a perforated film, or a film with transparent window regions can be provided, for example.

A simple possible embodiment provides that the resistor comprises a metal, preferably copper or a copper-nickel alloy. It is particularly advantageous if the resistor comprises a metal of which the electrical resistance drops under heating. To this end, PTC thermistors or PTC heating elements are proposed in order to attain a material-related regulation. This helps to avoid overheating of the blood in the oxygenator.

Further variants provide that the resistor comprises a plastic or carbon or graphite. An effective simple heat distribution in the oxygenator is achieved if the heating element comprises heating wires.

A distance of from 1 to 30 mm should be provided between the heating wire and the blood in order to avoid blood-critical temperatures. To this end, an insulation or heat distribution layer with a thickness of more than 1 mm can be provided.

The heating wires can be arranged for example in a spiraled manner or parallel to one another and are particularly preferably arranged evenly distributed in the housing chamber.

A simple variant that is suitable above all for cylindrical oxygenators provides that the oxygenator has a central opening with a mandrel-like holding element. The mandrel-like holding element can then also comprise the heating element so as to heat blood flowing in the housing chamber.

In accordance with the method the object of the invention is achieved by a method for controlling the heat emission at a heating element of an oxygenator, in which method the flow of blood through the oxygenator and the power of a pump influencing the flow rate are measured and the heating power is adjusted on that basis. Here, the heating element can comprise a plurality of heating sub-elements actuatable separately from one another, which heating sub-elements can be actuated such that the temperature difference between the temperature of the blood at the heating sub-element and the temperature of the heating sub-element does not exceed a predetermined value. These methods are suitable in particular for an oxygenator according to any one of the preceding claims.

Exemplary embodiments of oxygenators according to the invention are shown in the drawing and will be described in greater detail hereinafter.

Figure 2:
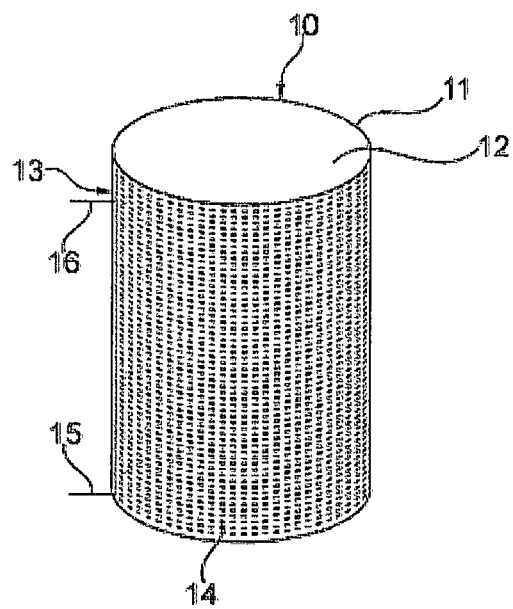
Figure 3:
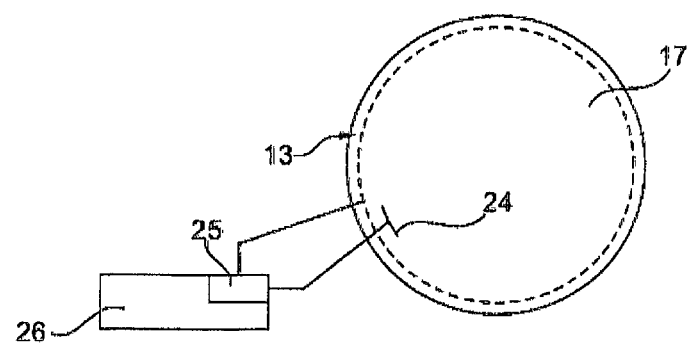
Figure 4:
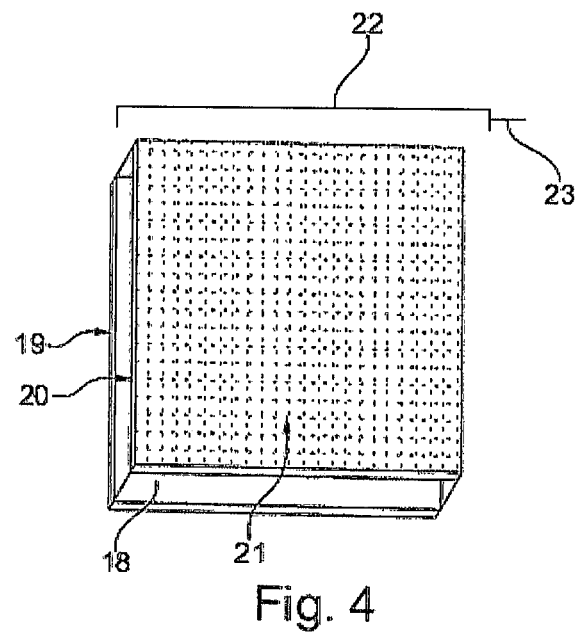
Figure 5:
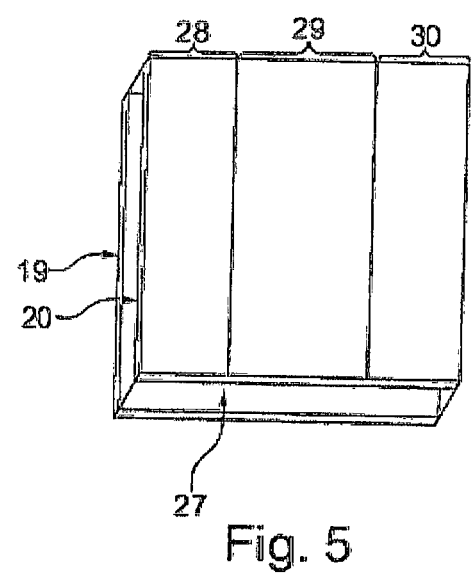
Figure 6:
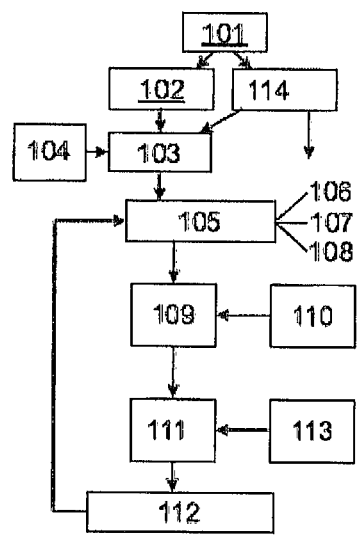
Figure 7:
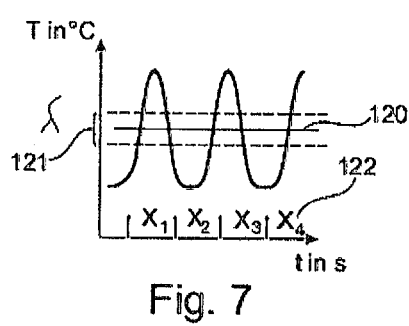
Figure 8:
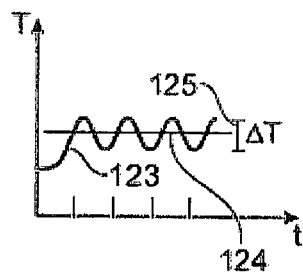
Figure 9:
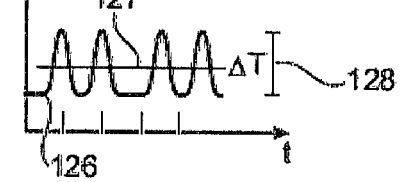

In the drawings:

FIG. 1 shows a known oxygenator with blood, gas and water flow;

FIG. 2 schematically shows an electrically heated oxygenator;

FIG. 3 shows a plan view of the oxygenator shown in FIG. 2;

FIG. 4 schematically shows an oxygenator with layered membrane fibre mats and net-like heating wires;

FIG. 5 schematically shows an oxygenator having layered mats and heating wires arranged in parallel;

FIG. 6 schematically shows the cooperation of components for an algorithm;

FIG. 7 schematically shows the mean temperatures over time;

FIG. 8 schematically shows the temperature over time at a first location; and FIG. 9 schematically shows the temperature over time at a second location.

The oxygenator 1 shown in FIG. 1 has a blood inlet 2 and a blood outlet 3. In order to supply gas, a gas inlet 4 and a gas outlet 5 are provided. In the heat exchanger, hollow fibres through which water is passed are provided in the radially inner region, and semipermeable hollow fibres through which gas is passed are provided in the radially outer region. Heating by means of water entering at the water inlet 8 and exiting at the water outlet 9 thus occurs radially inwardly, whereas in the radially outer region 7 a gas exchange takes place. Reference is made to EP 765 683 B1 with regard to a more detailed explanation of an oxygenator of this kind.

In the oxygenator shown schematically in FIG. 2, the primary design is substantially retained, and the water inlet 8, the water outlet 9 and the hollow fibres through which water is passed are omitted. The oxygenator 10 has a housing wall 11 which surrounds a housing chamber 12. This housing chamber 12, as shown in FIG. 1, has a blood inlet 2 and a blood outlet 3 and a gas inlet 4 and a gas outlet 5. A heating wire 14 arranged in the housing wall 11 and wound at uniform intervals around the housing chamber 12 is used as heating element 13. The heating wire 14 forms an electric resistor that generates heat if a voltage is applied at the electric connection 15, 16.

The oxygenator, as in the exemplary embodiments of FIGS. 1 to 3, can comprise wound hollow-fibre mats 17, which are arranged in the housing chamber 12, or, as shown in FIGS. 4 and 5, stacked mats 18 formed from hollow-fibre membranes, which are arranged between two plates 19 and 20. In the exemplary embodiment of FIG. 4, a wire structure 21 is incorporated in the plates in a net-like manner and is connected to an electric connection 22, 23. In the case of the net-like wire structure, current is applied in only one direction of the grid, i.e. from left to right or from top to bottom, and the other direction is used for heat conduction with another non-current-conducting material, or an insulation layer is provided between two current-conducting wires of the various directions and avoids a short circuit. FIG. 5 shows wrapped plates 19 and 20.

FIG. 3 schematically shows a temperature sensor 24 which is connected to a temperature control device 25 which is received in a console 26.

The heating element 27 shown in FIG. 5 consists of a plurality of schematically indicated heating sub-elements 28, 29 and 30, which can be actuated such that a certain temperature difference between the heating sub-element and blood temperature is not exceeded at the heating sub-element.

All heating wires are insulated so as to avoid an overheating of the blood and also direct contact between the heating wire and blood, and so as to distribute the emission of heat over a larger surface. This insulation can also be structured in order to improve the heat transfer.

FIGS. 6 to 9 show the algorithmic control after time intervals in an optimised form. A model is established from a real gas exchanger. In this gas exchanger model, which in FIG. 6 is shown as an oxygenator model 114 for measurement point localisation, measurement points are defined and the material properties that are required as parameters for the calculations are determined. The temperature can be measured at all measurement points.

Blood and gas parameters are fed into the console (KD) by the sensors already provided in an ECMO system. A desired temperature is then compared with a measured temperature under consideration of console values (KD). This is performed individually for each measurement point and each heating element. Various tolerances between measured value and desired temperature thus result. The appropriate heating frequency with heating incidence and heating intensity is then selected from all parameters for each heating element so as to reach the desired temperature and then maintain it so as to treat the blood as gently as possible. These frequencies can be stored in a table in order to later facilitate the control of the oxygenator.

In the algorithm shown in FIG. 6 the user 101 defines the desired temperature 102 that is input into the console 103. In addition, the blood flow, gas flow and pressure parameters 104 are input into the console. The console prompts a temperature measurement 105 in order to determine mean temperatures 106, 107 and 108 at different measurement points of the oxygenator. The comparison 109 of the desired temperature (WT) and the mean measured temperature at different locations leads to the difference value (AG). This value is set against the defined temperature deviations 110 at different locations and the console data (KD), such as the blood flow. This then gives the basis for individual control 111 of the heating elements on the basis of the reconciliation (AG) of the temperature deviations (AT) and the console data (KD). The heating elements 112 can be actuated using these values. In addition, the individual control can also be influenced by the heating algorithm 113, which is selected from a table and is given from the measured parameters.

The heat emission of the heating elements 112 affects the temperatures 105 measured by the temperature measurement, whereby a feedback to the measured temperatures is provided.

To this end, FIG. 7 shows the desired temperature 120 in a coordinate system with the temperature in ° C. over time in seconds. The lambda value indicates the heat conductivity, which is influenced by the material constants and which causes temperature peaks to be accommodated. For example, temperature measurement points 122 are denoted by x1, x2, x3 and x4.

FIGS. 8 and 9 show the temperature curve over time for two measurement locations. Here, the temperature curve 123 over time at a first measurement location is shown in FIG. 8 as a wavy line which fluctuates around a temperature 124 and defines a delta T (ΔT) 125. FIG. 9 correspondingly shows, at a second location, the actual temperature 126 as compared to a mean temperature 127, whereby a temperature deviation delta T (ΔT) 128 results.

The invention claimed is:

1. An oxygenator (10) with a housing wall (11), defining a housing chamber (12) with a blood inlet (2), a blood outlet (3), a gas inlet (4) and a gas outlet (5), a heating element (13) which has an electric resistor (14) and is arranged in the oxygenator between the blood inlet (2) and blood outlet (3) in order to control the temperature of the blood flowing through the housing chamber (12), an electric connection (15, 16) and a temperature control device (25), wherein the heating element (13) delivers a different heating power at different locations in the housing chamber (12).

2. The oxygenator according to claim 1, wherein the heating element (13) is arranged in the housing chamber (12).

3. The oxygenator according to claim 1, wherein the heating element (13) is arranged in the housing wall (11).

4. The oxygenator according to claim 1, further comprising membranes.

5. The oxygenator according to claim 1, further comprising an encapsulation layer for holding fluid lines, and the heating element (13) is arranged in the encapsulation layer.

6. The oxygenator according to claim 1, further comprising at least one temperature sensor (24).

7. The oxygenator according to claim 1, wherein the temperature controller (25) sets or controls the temperature of the heating element (13) individually at various locations.

8. The oxygenator according to claim 1, wherein the heating element (13) has a plurality of heating sub-elements (28, 29, 30) positionable at various locations of the oxygenator.

9. The oxygenator according to claim 8, wherein the heating element (27) has a plurality of heating sub-elements (28, 29, 30) actuatable separately from one another.

10. The oxygenator according to claim 1, wherein the heating element (13) is arranged in the oxygenator between the gas inlet (4) and gas outlet (5) in order to also control the temperature of gas flowing through the housing chamber (12).

11. The oxygenator according to claim 1, further comprising a heat-conducting arrangement for conducting heat to the heating element (13).

12. The oxygenator according to claim 1, further comprising a heat-conducting arrangement for distributing heat from the heating element (13) in the housing chamber (12).

13. The oxygenator according to claim 1, further comprising an insulation layer in order to insulate blood flowing in the housing chamber.

14. The oxygenator according to claim 13, wherein the layer is transparent or partially transparent.

15. The oxygenator according to claim 1, further comprising a reflection layer in order to reflect heat radiation from blood flowing in the housing chamber.

16. The oxygenator according to claim 1, wherein the resistor (14) is a metal.

17. The oxygenator according to claim 1, wherein the resistor (14) comprises a plastic or carbon or graphite.

18. The oxygenator according to claim 1, further comprising a central opening with a mandrel-shaped holding element.

19. The oxygenator according to claim 18, wherein the mandrel-shaped holding element comprises the heating element.

20. A method for controlling the heat emission at the heating element (13) of the oxygenator (10) according to claim 1, in which the flow rate of blood through the oxygenator (10) or the power of a pump influencing the flow rate are measured and the heating power is adjusted on this basis, wherein the heating element (13) delivers a different heating power at different locations in the housing chamber (12) of the oxygenator (10).

21. The method according to claim 20, wherein the heating element (13) has a plurality of heating sub-elements (28, 29, 30) actuatable separately from one another, which are actuated such that the temperature difference between the temperature of the blood at the heating sub-element (28, 29, 30) and the temperature of the heating sub-element (28, 29, 30) does not exceed a predetermined value.

* * * * *